United States Patent [19]

Schwaiger et al.

[11] 4,054,141
[45] Oct. 18, 1977

[54] ABSORPTIVE MATERIAL FOR HYGIENIC PURPOSES

[76] Inventors: Julius Schwaiger, Hirschbergerstr. 33, 8500 Nurnberg; Wolfgang Bracke, Triebweg 123, D-7000 Stuttgart-Feuerbach; Roland Bergel, Grafstr. 119, D-8000 Munich; Gerhard Wagner, Mogeldorfer Haupstr. 60, D-8500 Nurnberg, all of Germany

[21] Appl. No.: 772,451

[22] Filed: Feb. 28, 1977

[30] Foreign Application Priority Data

Apr. 6, 1976 Germany .............................. 2625177

[51] Int. Cl.² .......................................... A61F 13/16
[52] U.S. Cl. .................................. 128/287; 428/218; 428/290; 128/284; 128/296; 128/290 R
[58] Field of Search ................... 128/284, 287, 290 R, 128/296, 209 P; 428/290

[56] References Cited

U.S. PATENT DOCUMENTS

| 3,004,868 | 10/1961 | Sumner et al. ............... 480/290 |
| 3,395,201 | 7/1968 | Kalwaites ............... 128/290 R X |
| 3,545,441 | 12/1970 | Gravdahl ............... 128/287 |
| 3,759,775 | 9/1973 | Shepherd ............... 428/290 |
| 3,821,146 | 6/1974 | Drelich ............... 428/290 |
| 3,825,007 | 7/1974 | Rand ............... 128/296 |
| 3,848,598 | 11/1974 | Mesek ............... 128/287 |
| 3,888,256 | 6/1975 | Studinger ............... 128/296 |
| 3,903,890 | 9/1975 | Mesek ............... 128/287 |
| 3,939,836 | 2/1976 | Tunc ............... 128/290 W |
| 3,952,124 | 4/1976 | Mesek ............... 428/290 |

FOREIGN PATENT DOCUMENTS 2,041,354  8/1972  Germany .............................. 128/287

*Primary Examiner*—Aldrich F. Medbery
*Attorney, Agent, or Firm*—William Isler

[57] ABSTRACT

Fluid absorptive bodies for hygienic purposes or the like are formed consisting of an absorptive layer of hydrophil fibers, and a sheath formed at least in part of hydrophil fibers bound together by solid particles of thermoplastic. The hydrophil fibers of the sheath, at least in part, extend into the absorptive layer and the concentration of thermoplastic particles in the sheath decreases steadily from the exterior surface of the sheath to the interior of the absorptive layer. For the purpose of manufacturing such absorptive bodies, a process s preferably employed in which the inner surfaces of a mold corresponding to the contours of the absorbent body are coated with a layer of hydrophil sheathing fleece fibers and solid thermoplastic binder, the mold is filled with absorptive material, and the entire filling is heated, at least to the surface, to the binding temperature of the thermoplastic binder.

5 Claims, 4 Drawing Figures

ABSORPTIVE MATERIAL FOR HYGIENIC PURPOSES

The invention concerns an absorptive material ("suction body") for hygienic purposes, which consists of an absorptive layer and a sheath, formed at least in part of hydrophil fibers reinforced with plastic, and a process for its production.

Absorptive materials for hygienic purposes are used, for example, as sanitary napkins, foot pads ("step inlays"), bandages, hospital pads, but also as shoe inlays, dress shields and the like. For their production, cellulose flakes (flock) are generally used, but other materials are also possible, such as foam material flakes, granulates of material that swells, crepe paper foils, etc. These inherently absorptive materials are formed, by means of suitable apparatus, to an absorptive material, and, as a rule, slightly compressed. The absorptive body must then be surrounded by a sheath which has, on the one hand, the purpose of holding the fibers together, but which, on the other hand, must hinder as little as possible the passage of the fluid to be absorbed. As sheath, net tubings were often used, formerly, but these can only be used with sheet-form absorptive materials. With fiberform absorptive materials, thus, in particular, cellulose flakes, usually plastic-bound fleeces are used today, which are used with a fabrication of the absorptive material in the form of endles strips and then, generally, cut up, suitably, together with the absorptive material.

The use of such plastic-bound fleeces has advantages, but also disadvantages not to be overlooked. The disadvantages consist of the fact that it is difficult to adapt the fleece lines to such absorptive materials without folds, of which the cross section is different at different points of the absorptive material. Another disadvantage is that the fleece sheaths represent a considerable barrier to the fluid to be absorbed.

In the literature, therefore, for example, in German Disclosure No. 24 23 175, absorptive materials have been described in which a separate sheath is omitted and which contain gluestuffs suitable for surface sealing, for example, liquid resins. A similar proposal is contained also in German Disclosure No. 25 36 925. The use of liquid (fluid) resins for the surface binding of the fibers of a hygienic absorptive material has considerable disadvantages, however. These consist of the fact that it is generally not possible to distribute the liquid glues, to be applied in drop form, in such manner that the fibers are glued only at their contact points. Rather, the danger exists that liquid glues will run together in considerable zones, because of the capillary forces prevailing there, and thus stop up the interspaces between the fibers, thus between the fibrillae, and thus considerably reduce the absorption power of the fibers. These disadvantages have all the stronger effects when in the later application of the liquid glues, precisely the surface, so important to the rate of absorption, is coated especially thickly with liquid glue.

In the German Disclosure No. 25 20 899, an absorptive material to be used as a tampon is described, which consists of hydrophil absorptive fibers, bound with suitable binders in the form of a three-dimensional net, and thus strengthened. As binders are proposed there, among others, thermoplastic glues in powder or fiber form. The suggestion is made there, however, apparently because the three-dimensional binding sought there, including all the material, necessitates an even distribution of the glue in the absorptive material. Such an even distribution is apparently easier to obtain, however, with solid substances than with liquid substances. The problem there is differently situated, therefore, than the present problem, which consists of the production of absorptive materials which consist of an absorptive layer as well as a sheathing layer formed of hydrophil fibers.

The invention addresses itself to the problem of proposing an absorptive material for hygienic purposes, which consists of an absorptive layer and a sheath formed, at least in part, of hydrophil fibers reinforced with plastic, and in which, on the one hand, the sheathing layer is practically no barrier to the fluid to be absorbed, and in which, on the other hand, the sheath hugs the absorptive material completely without folds.

This problem is solved, according to the invention, by the fact that the hydrophil fibers of the sheath are bound together through thermoplastic solid particles, especially fibers. It is advantageous, here, if the proportions are chosen so that the concentration of solid thermoplastic particles in the sheath decreases steadily from the surface of the absorptive material to its interior. To obtain an especially intimate anchoring of the sheath so produced in the absorptive material, and thus an especially good rate of absorption, it is proposed that the hydrophil fibers of the sheath extend at least partly into the absorption layer. In this way, the so-called "wick" effect is utilized in the present case also, in the known way. However, it should be emphasized, as important to the invention, that solid particles are used for the binding of the hydrophil fibers of the sheath. In this way, it is assured that actually, only a binding of the fibers and thus the desired strengthening, is obtained, without the glue being able to penetrate inside the fibers or otherwise stop up the capillaries necessary for the absorption and storage of fluid.

For the production of such absorbent materials, a process is proposed which is distinguished by the fact that first the whole inner surface of a mold corresponding to the contours of an absorptive body, is coated with a layer of hydrophil sheathing fleece fibers and solid thermoplastic binder; then the mold is filled with absorptive material, and the entire filling is heated, at least at the surface, to the binding temperature of the thermoplastic binder. The process may be carried out, to advantage, on continuously operating machines, known per se, of which the mold consists of two drums, of which the mantle surfaces roll down, one on the other. Details about this will be given in the description of the figures.

The process proposed may be used when absorptive materials are to be produced which are provided on all sides with a continuous sheath. For many purposes, however, it is better to provide the absorptive material only partly with such a sheath or covering, and to make other parts of a foil impermeable by fluid. In this case, the procedure may be such that only the part of the mold corresponding to the later use side of the absorptive material, is coated with a thin layer of sheathing fleece fibers; then the mold is filled with absorptive material, covered with a thin foil (film) of thermoplastic material, and the whole filling is then heated, at least at the surface, to the binding temperature of the thermoplastic binder. Proceeding in this way, there is at the same time a binding of the sheath produced with the thermoplastic foil introduced, so that the production of other glued places is not necessary.

The invention is explained below with reference to the attached drawings.

Figure 1:
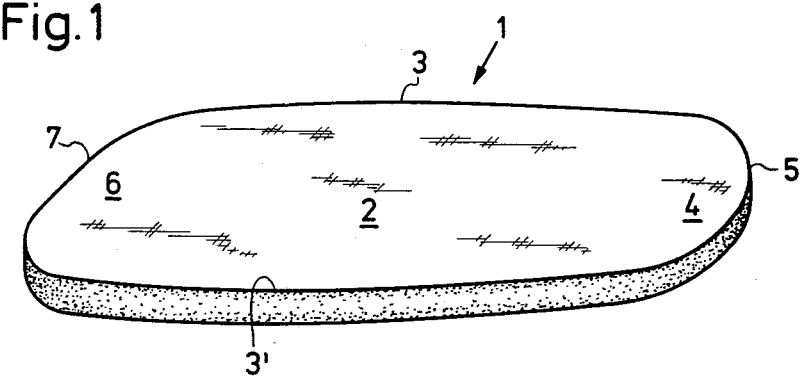
FIG. 1 shows a perspective view of an absorptive material suitable for the production of sanitary napkins.

FIG. 1 shows that the absorptive material 1 has a very irregular contour. The absorptive material consists, in the example shown, of a middle piece 2 with edges 3 and 3' running approximately parallel with each other. The middle piece is joined at one end with an end piece 4, of which the edges 5 are rounded, and at the other end with a front piece 6, of which the contour 7 is pointed. In all parts of the absorptive material, the sheath, which cannot be seen in FIG. 1, hugs the absorptive material quite tightly and without a fold, the sheath passing, practically continuously, into the absorptive body itself, and is thus firmly bound with it.

Figure 2:
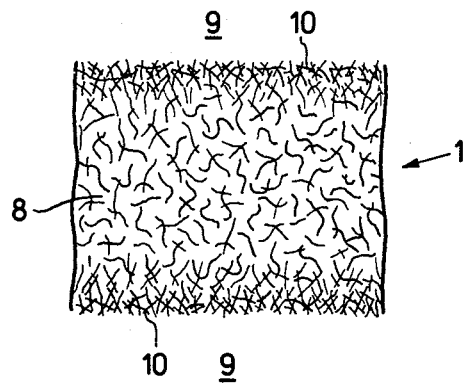
FIG. 2 is a greatly enlarged schematic cross-section view through a part of the absorptive material according to FIG. 1.

To illustrate these relationships, there is shown in FIG. 2, a greatly enlarged diagram of the cross-section of a part of FIG. 1. From this representation, it can be seen that the absorptive material 1, in the example shown, which forms the usual case, consists of hydrophil fibers 8 laid at random, which are joined to the surface 9, in each case, with the aid of thermoplastic particles 10. As already mentioned, the fibers 8 may be replaced, wholly or in part, by other suitable absorptive materials, such as foam material flakes, swelling materials, in powder or granulated form, etc. The thermoplastic particles 10 may be present in the form of powder particles or fibers.

FIG. 2 shows, through its schematic representation, that the concentration of the thermoplastic particles 10 decreases from the surface 9 to the interior of the absorptive material. This is represented schematically by the fact that the density of the lines 10, which symbolize the thermoplastic particles, decreases from the surface to the interior. There results in this way, on the one hand, a concentration gradient of the binder, which assures a uniform anchoring of the reinforced surface layer in the interior of the absorptive material, and on the other hand, the possibility for the hydrophil fibers to reach from the sheathing layer into the inside of the absorptive material and thus, in the matter of a wick, to conduct the fluid occurring outside rapidly to the inside.

Figure 3:
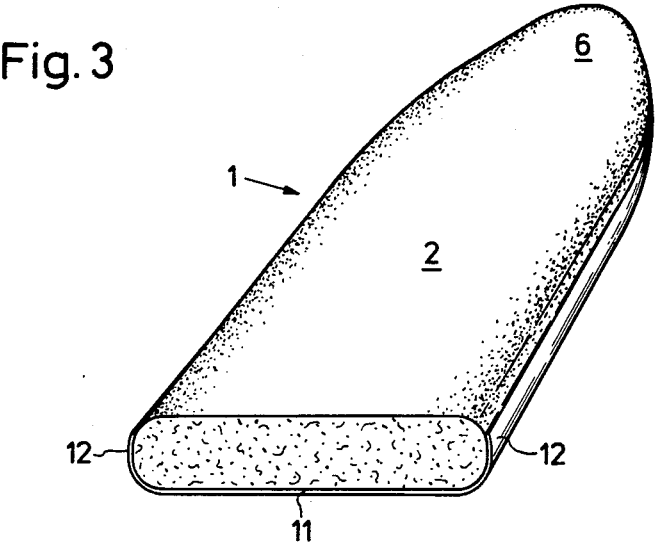
FIG. 3 is a perspective view of an absorptive material suitable for the production of sanitary napkins, of which the under side is covered with a thermoplastic foil.

FIG. 3 represents an absorptive body 1, which has a similar form to that in FIG. 1. Only the end piece 4 is cut off. The representation shown that this absorptive body has also a foil layer 11, which covers the under surface completely. The foil (film) layer 11 is brought around the absorptive body, in the known way, on the edges 12, so that an especially good sealing results there (roof-channel, gutter effect).

Figure 4:
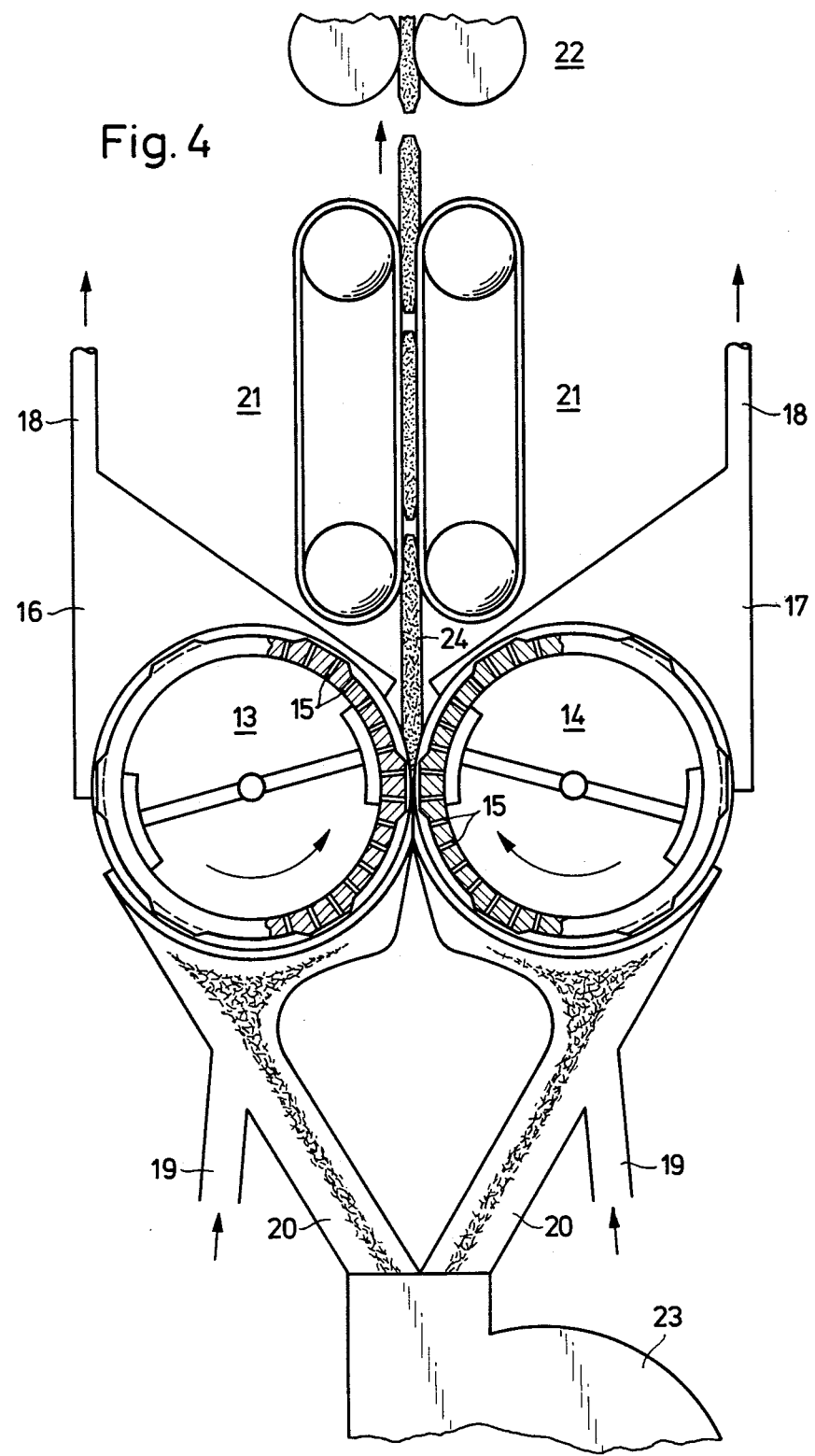
FIG. 4 is a schematic cross-section through a device which is suitable for carrying out the production process.

Absorptive materials of the kind proposed may be produced, for example, with an apparatus according to FIG. 4. Such apparatus is known, in principle, and described, for example, for the production of other absorptive bodies, in German Pat. No. 2,041,354.

The apparatus shown in FIG. 4 consists of the two forming (mold) drums 13 and 14, which roll down, one on the other, by their contoured mantles. The mantle surfaces are provided with radial bores 15, so that air can flow through them.

The two forming drums 13 and 14 run in suction boxes 16 and 17, which are connected at 18, in each case, to a suction pump, not shown.

To the end (on the side) opposite the suction boxes, there are several flock (flake) feed channels. The channels 19 serve for the pre-filling of the mold hollows with a mixture of sheathing fleece fibers and solid thermoplastic binder, and the channel 20 serves for the filling of the mold hollow, in the known way, with absorptive material.

On the outlet side (end) of the apparatus are several conveyor belts 21, indicated schematically, which carry away the absorptive bodies and introduce them into the pressing stations 22 which are connected next.

With the aid of this apparatus, the process proposed is carried out as follows

The mold, corresponding to the contours of the absorptive body, consists of the two forming drums 13 and 14, rolling down one on the other. Before the mold parts, fitting each other, come together, there are coated, through the channels 19, with a layer of hydrophil sheathing fleece fibers and solid thermoplastic binder. Since the covering takes place by the air-laying process, it is substantially uniform and can also be adjusted in its thickness. As soon as the coating has taken place sufficiently, the mold drums move on and the mold is filled, through the channel 20, with absorbent material, for example, cellulose flakes. The cellulose flakes (flock) are fed, in the known way, to the channel 20 through a feed blower 23, which may be a part of the fiber-separating apparatus. As soon as the two halves of the mold have been sufficiently filled, one is set on the other and the formed bodies 24 are compressed under light pressure and finally discharged to the conveyor belts 21. The formed bodies are still relatively sensitive in this condition. They are picked up by the conveyor belts 21 and carried to a first pressing station 22. This pressing station may consist of heated strips or rolls, but it may be formed in any other way. It has also proved advantageous to arrange several pressing stations one after another, in which, for example, the wide surfaces of the formed bodies are compressed first and then the narrow side surfaces are additionally compressed.

The heating of the surface may take place in any known way, by radiation and finally also by dielectric heating. Which process is applied, depends on the details of the case. Experiments have shown that in all cases, formed bodies of the highest quality with ideal absorption performance result.

Having thus described our invention, we claim

1. An absorptive body pad for contact with the human skin for hygienic purposes, said body pad having at least one skin contacting surface layer portion and a porous central portion, said central portion comprising randomly dispersed hydrophillic fibers and surface layer portion being porous and comprising fibers at least some of which are hydrophobic, said layer fibers having dispersed therethrough a gradually diminishing quantity of solid thermoplastic particles from the top of the layer to its bottom, which particles when subjected to heat form a dense porous skin-like surface, at least some of said layer fibers adjacent the bottom extending into and engaging with the fibers of said central portion, thereby defining a unitary absorptive body contacting pad.

2. The body pad of claim 1 wherein said dispersed particles are more concentrated at the outer part of the surface portion than the inner part of the surface portion defining a porous pad that is progressively more dense at the surface than in the central portion.

3. The body pad of claim 1 wherein the surface opposite the body contacting surface is covered with a thin foil layer.

4. The body pad of claim 1 wherein the solid thermoplastic particles are in flake form.

5. The body pad of claim 1 wherein the solid thermoplastic particles are in granulated powder form.

* * * * *